United States Patent [19]

Kelly et al.

[11] Patent Number: 4,666,879
[45] Date of Patent: May 19, 1987

[54] EXTRUDED COPPER CHROMITE-ALUMINA HYDROGENATION CATALYST

[75] Inventors: Donald G. Kelly, Parma Heights; Eugene Nebesh, Parma, both of Ohio

[73] Assignee: Harshaw/Filtrol Partnership, Cleveland, Ohio

[21] Appl. No.: 774,830

[22] Filed: Sep. 11, 1985

[51] Int. Cl.$^4$ .............. B01J 21/08; B01J 23/26; B01J 23/72

[52] U.S. Cl. .................... 502/244; 502/306; 502/318

[58] Field of Search ............. 502/306, 318, 244

[56] References Cited

U.S. PATENT DOCUMENTS

| | | | |
|---|---|---|---|
| 2,741,618 | 4/1956 | Young | 260/290 |
| 2,795,600 | 6/1957 | Chitwood et al. | 260/465.1 |
| 3,630,670 | 12/1971 | Bell et al. | 23/143 |
| 3,781,406 | 12/1973 | Roth et al. | 423/213.2 |
| 3,787,322 | 1/1974 | Koberstein et al. | 502/318 X |
| 3,855,388 | 12/1974 | Rosinski | 502/318 X |
| 3,883,445 | 5/1975 | Roth et al. | 252/462 |
| 3,925,490 | 12/1975 | Reich et al. | 260/643 |
| 3,928,236 | 12/1975 | Rigge et al. | 252/463 |
| 4,124,537 | 11/1978 | Gembicki et al. | 252/465 |

FOREIGN PATENT DOCUMENTS 80922 5/1976 Poland .
598633 3/1978 U.S.S.R. .

OTHER PUBLICATIONS

Article—Mechanism of Hydrogenation of Furfural over an Aluminum-Copper-Chromium Catalyst—Kuzina, et al.

*Primary Examiner*—W. J. Shine
*Attorney, Agent, or Firm*—James A. Lucas

[57] ABSTRACT

An extruded copper chromite-alumina catalyst is prepared by blending together from 40-82% by weight of copper chromite and 18-60% of an extrudable alumina, typically having a pseudoboehmite or α hydroxy boehmite structure. The extruded catalyst after calcining is useful for the liquid and vapor phase hydrogenation and hydrogenolysis of various carbonyl compounds and the functional side groups of aromatic compounds.

The extruded catalyst is characterized as having a surface area of between 20 and 225 square meters per gram and a packed apparent bulk density of between about 0.70 and about 1.20 g/cc.

16 Claims, No Drawings

EXTRUDED COPPER CHROMITE-ALUMINA HYDROGENATION CATALYST

BACKGROUND OF THE INVENTION

Hydrogenation involves the addition of molecular hydrogen to the unsaturated bonds of organic compounds. Nearly all such reactions require the presence of a catalyst to initiate, to sustain or to facilitate the reaction.

Copper chromite catalysts have been used for many years to hydrogenate carbonyl compounds and functional side rings of aromatic compounds. Following are some of the typical classes of reactions in which copper chromite catalysts are employed:

1. The hydrogenation of aldehydes to their corresponding alcohols. These reactions are usually carried out in liquid phase at a pressure of between 1 and 10 atmospheres and a temperature of between 120° C. and 160° C.

2. Conversion of fatty acids or methyl esters of fatty acids to saturated fatty alcohols. These are typically carried out as slurry phase or fixed bed trickle phase reactions at temperatures between 250° C. and 300° C. and pressures of between 170 and 300 atmospheres.

3. Hydrogenation of furfural to furfuryl alcohol. This is a liquid phase reaction, using a barium stabilized copper chromite catalyst, typically conducted at 50 atmospheres pressure and a temperature between 160° C. and 200° C. If carried out as a trickle phase reaction, a pressure of about 14 atmospheres and a temperature of about 170° C. is used.

DISCUSSION OF PRIOR ART

There are a number of patents describing catalysts and catalyst mixtures containing copper, chromium and alumina. Generally, however, these involve the copper and chromite deposited on an alumina support. U.S. Pat. No. 2,741,618 describes such a catalyst for use in the production of pyridine from pyrans using a catalyst comprising 93–99% activated alumina, 0.5–5% copper, 0.2–2.0% chromium and less than 0.1% of an alkali metal sulfate.

U.S. Pat. No. 2,795,600 describes a chromium promoted copper and activated alumina catalyst containing less than 10% of calcium, barium, lithium or strontium useful for the production of nitriles by the vapor phase reaction of primary alcohols and ammonia.

U.S. Pat. No. 3,781,406 and 3,883,445 describe an auto exhaust catalyst containing 2–15 parts by weight of copper, 0.1 to 10 parts by weight chromium and 1–15 parts of a rare earth metal on 100 parts of an alumina support. The alumina is a transition alumina, preferably gamma alumina and is in the form of an extrudate or the like.

BRIEF DESCRIPTION OF THE INVENTION

This invention relates to an extruded copper chromite catalyst prepared from between about 40% and about 82% by weight of copper chromite and about 18% and about 60% of a highly dispersible alumina ($Al_2O_3$), typically having a pseudoboehmite or an $\alpha$ hydroxy boehmite structure. The catalyst has a surface area of between about 20 and about 225 square meters per gram, a packed apparent bulk density of between about 0.70 and about 1.20 g/cc, and a crush strength which is adequate for industrial applications.

The extruded copper chromite catalyst is useful in a number of hydrogenation reactions, said reactions being conducted in the vapor phase, trickle phase or liquid phase at elevated temperatures and pressures. A minor amount of a stabilizer such as manganese or barium may be added to the catalyst to inhibit the in situ reduction of the copper.

The present catalyst has several advantages over the prior art catalysts, among them being (a) lower catalyst cost. The replacement of up to 60% of higher cost copper chromite with lower cost alumina results in a diminution in the per pound catalyst cost. A further savings is realized because the lower density of the alumina decreases the total weight of the catalyst charge to the reactor. Yet another cost advantage is realized by the lower cost of extruding versus tabletting.

(b) lower pressure drop due to packing factor of the catalyst. At equal nominal particle diameters, the pressure drop for the extrusions at a typical length to diameter (L/D) ratio of 2–4 would be 25% to 40% less than that of tablets. At particle sizes such that equal external (geometric) catalyst areas are charged into a reactor, the extrusions would generate a pressure drop about 60% that of tablets. Extrusions with a nominal particle diameter one half that of tablets can be run with no increase in pressure drop.

(c) an activity at least comparable to that of tabletted catalysts having the same composition and size, but without the alumina. When compared to standard copper chromite hydrogenation catalysts, the activity of this novel catalyst is better.

(d) less diffusion limitation thereby readily permitting the hydrogen gas and the hydrocarbons to penetrate more completely into the interior of the catalyst to reach the active catalyst sites.

(e) more flexibility in terms of catalyst size and shape. The ability to extrude the catalyst in a variety of diameters and shapes, i.e. cylindrical, fluted, tubular, etc., increases the choices that the catalyst user has with respect to pressure drop, catalyst activity and other reaction conditions. Furthermore, the smallest practical size that can be achieved with a conventional tabletting machine is $\frac{1}{8}''$ whereas extrusions as small as 1/32" in diameter are achievable.

DETAILED DESCRIPTION OF THE INVENTION

This invention relates to a copper chromite catalyst prepared from a blend of between about 40% and about 82% copper chromite and between about 18% and about 60 weight % of an extrudable form of alumina. The alumina typically has a pseudoboehmite or $\alpha$ hydroxy boehmite structure.

More particularly, the invention comprises an extruded catalyst containing copper chromite and alumina, said catalyst composed, on a weight basis, of between about 60% and about 80%, preferably between about 68% and about 72% of copper chromite and between about 40% and about 20% and preferably between about 32% and about 28% of alumina derived from an extrudable precursor. The copper chromite typically exists in a spinel structure and is represented by the formula $CuO \cdot CuCr_2O_4$. It includes combinations wherein the ratio of melts typically may vary from 1.2 to 4.67 parts by weight copper to 1 part of chromium.

The blend of copper chromite and alumina is readily extrudable into any number of catalyst shapes and sizes.

For example it can be extruded into a trilobe such as that covered by U.S. Pat. No. 4,517,077; a cylindrical shape with a hollow interior and one or more reinforcing ribs such that covered by U.S. Pat. Nos. 4,510,263 and 4,089,941; rectangular and triangular shaped tubes such as those covered in U.S. Pat. No. 4,441,990, cloverleafs, cross and C-shapes such as those covered in U.S. Pat. No. 3,764,565 and many other shapes.

The invention also includes the method of preparing the catalyst comprising blending between about 40% and about 82% copper chromite with from between about 18% and about 60% (as $Al_2O_3$) of pseudoboehmite or α hydroxy boehmite alumina, between about 3% and 7% of nitric acid based on 100 parts of $Al_2O_3$ in the catalyst blend, and water to make an extrudable mix, followed by extruding the mix and drying and calcining the extrudate. Instead of nitric acid, other mineral acids such as HCl or $H_2SO_4$, organic acids such as formic acid or acetic acid or bases such as ammonium hydroxide may be used to peptize the alumina. The calcination converts the alumina from a transitional state as a pseudoboehmite or α hydroxy boehmite to a gamma, alpha or other crystalline form of alumina.

Following calcination but before use, the catalyst normally is activated by reducing some of the copper chromite and the cupric oxide. The reduction step may be carried out in situ immediately prior to use. Alternatively it may be carried out in advance of use by contacting with hydrogen at elevated temperatures according to well-known procedures, in which portions or all of the copper oxide and copper chromite are present in the reduced state. The reduced catalyst may then be stabilized, e.g. by exposing the catalyst to air to form a thin oxide layer on the surface, or it may be stored in a protective medium until use.

Of particular importance in the teachings of the invention is the use of an alumina which will facilitate extrusion of the catalyst mix while at the same time synergistically maintaining the hydrogenation activity of the catalyst on an equal volume or improving the activity on an equal weight basis. Most aluminas containing at least 10% chemically combined water will be found to be useful replacements for a portion of the copper chromite. For the purpose of the present invention, pseudoboehmite alumina and α hydroxy alumina have been found to be particularly suitable. Pseudoboehmite alumina refers to an alumina, regardless of the manner of preparation, which, when dried at 140°–160° C. for a period of 1 hour has a loss on ignition (LOI) at 1000° C. for 1 hour from about 20% to about 50% by weight, and which exhibits an X-ray diffraction peak in the 6.5–6.8 angstrom range. Any alumina containing at least 25% of that structure is considered to be pseudoboehmite. One method of preparing alumina with this structure is taught in U.S. Pat. No. 3,630,670. Various pseudoboehmite aluminas are commercially available such as certain members in the Versal family of aluminas sold by Kaiser Aluminum & Chemical Corporation and Catapal aluminas sold by Vista Chemical Company.

Pseudoboehmite aluminas are readily dispersible in an acid medium as colloidal size particles. The acid dispersibility and colloidal size contribute to their ease of extrusion. These aluminas generally have a surface area in the range of about 250 to about 300 $m^2/g$.

The catalyst of this invention is useful in a number of high temperature chemical reactions including but not limited to hydration, dehydration, and hydrogenolysis. Among the specific uses of the catalyst is the hydrogenolysis of dimethylcyclohexane dicarboxylate to the corresponding alcohol; hydrogenation of 2-ethyl hexanal to 2-ethyl hexanol; hydrogenation of n-butyl aldehyde and other oxo aldehydes to oxo alcohols; reductive amination of secondary alcohols with alkyl amines to form tertiary amines; the conversion of fatty alcohols to acids, the hydrogenation of furfuryl aldehyde to alcohol, the hydration of acrylonitrile to acrylamide, and the conversion of primary amines to secondary amines.

The copper chromite is prepared by conventional techniques for example by mixing the soluble salts such as the nitrates or acetates of copper and chromium followed by precipitation, filtering, washing, drying and calcining. Alternatively, copper oxide and chromium oxide may be blended together as an aqueous slurry with ammonium hydroxide. The copper chromite is recovered as a fine granular powder having a surface area of between about 20 and about 120 $m^2/g$. Seventy (70) parts by weight of the copper chromite powder is dry mixed with 30 parts pseudoboehmite alumina after which between about 3% and about 7% nitric acid (based on 100 parts of $Al_2O_3$ in the catalyst mix) and water are added to form an extrudable mix. The mix is extruded through the orifice of an extrusion die, is dried at 180° C. to 200° C., and is then calcined at a temperature of between 380° C. and 925° C.

The catalyst may be prepared by other techniques as well. For example, the copper and chromium may be added as oxides or as the soluble or insoluble salts to the alumina extrusion mix, followed, if necessary with a drying step before extrusion. Yet another option is to form a slurry of the copper, chromium and alumina as oxides, soluble salts, insoluble salts or mixtures of these followed by filtering and drying as needed to form an extrudable mix.

If it is desired to chemically stabilize the catalyst composition to prevent unnecessary reduction of the copper, a minor amount, preferably between 2% and 6%, of a stabilizing agent such as barium or manganese, is added to the initial slurry of copper oxide and chromium oxide. These stabilizing compounds may be added to the mix in the form of the nitrate or in some other soluble or insoluble form.

In a preferred embodiment of the invention, a commercially available copper chromite catalyst, sold by Harshaw/Filtrol Partnership as Cu 1180 P, is used as the starting material for the preparation of the extrudable catalyst. This starting material is a powdered barium stabilized catalyst useful in slurry phase hydrogenation. A typical composition of the catalyst is 43% CuO, 45% $Cr_2O_3$ and 9% BaO. The catalyst has a surface area of about 110 $m^2/gm$ and a packed apparent bulk density of about 0.8 g/cc. Between 40 and 82 parts by weight of this catalyst is combined with between 60 and 18 parts by weight of a pseudoboehmite aluminum oxide such as Kaiser's Versal 250 in a blender such as a Littleford Lodge or a mix muller along with between 3 and 7 weight percent of nitric acid to peptize the mix, and sufficient water to give a loss on ignition during calcination of 37%–39%. The peptized solution is expressed through an extrusion orifice between 1/32" and ⅛" to form an extrudate having a cylindrical, fluted or other appropriate shape. The extrudate is dried on a belt drier between 180° and 200° C. and is then calcined at 380° to 420° C. in a gas fired elevator furnace, rotary kiln or the like.

Typical properties for this novel extruded catalyst are as follows:

Surface area—125-225 square meters per gram, as determined by the single-point BET method, Helium density—4.36 g/cc as determined on a Helium-Air Pycnometer, an instrument useful for determining the density of the skeleton of a porous material, Mercury density—1.74 g/cc as measured at 11.5 psia with an Aminco 15,000 psig Porosimeter, Pore volume—in cc per gram is measured using a Quantachrome Autoscan Porisimeter
  Up to 120 angstrom in diameter—0.169
  200 angstrom in diameter—0.265
  350 angstrom in diameter—0.29
  600 angstrom in diameter—0.30
  1000 angstrom in diameter—0.32
  10,000 angstrom in diameter—0.344
  152,000 angstrom in diameter—0.35

Apparent bulk density—1.15 g/cc packed, measured by filling a graduated cylinder in small increments and tapping the cylinder gently on a soft surface after each addition until a constant volume is obtained.

Average crush strength—11.3 pounds as measured by pressing a single ⅛" extrudate having a ⅛" length between two parallel plates.

Attrition—2.5 weight percent at 30 minutes

Analytical composition—
  Cu—25.9%
  Cr—23.5%
  Ba—6.4%
  $Al_2O_3$—24.6%

The following two examples illustrate typical reactions comparing the catalyst of the present invention with prior art catalysts in catalytic hydrogenation reactions. In both examples, the catalyst was prepared from Cu-1180 P which was mixed with 30% pseudoboehmite alumina oxide in a Littleford Lodige blender along with 5% nitric acid and sufficient water to make an extrudable mix. The mix is extruded, followed by drying at 180°-200° C. and calcining at 380°-420° C. The calcined extrudate has a surface area of between 125 and 140 $m^2/g$ and a packed apparent bulk density of between 0.95 and 1.0 g/cc.

EXAMPLE I

The catalyst of the present invention was used to catalytically hydrogenate a typical long chain oxo aldehyde to its corresponding alcohol. In this particular instance, the feedstock was 2-ethylhexanal. Various sizes and shapes of extrudates were compared with one another and with a commercially available barium stabilized copper chromite catalyst having the following composition: 36% CuO, 40.5% $Cr_2O_3$, 8.5% BaO, and other inerts/binders. The properties of this commercial catalyst are as follows: Apparent bulk density 105 pounds per cubic foot; Crush strength—18 pounds, Surface area as determined by the single point BET method—35 square meters per gram; and Pore volume—0.10 cc per gram.

The test conditions are as follows:
  Pressure—1000±100 psig
  Temperature—150°±2° C.
  Catalyst charge—6.27 grams
  Feed charge—447.7 grams
  Reaction time—2 hours In all instances, the catalyst charge represented 1.4% by weight of the feed charge.

All of the catalyst samples of the present invention, except as noted, were composed of 70 parts by weight copper chromite and 30 parts by weight of Versal 250 alumina. This alumina has a surface area of 300 $m^2/gm$ and a loose bulk density of 18 $lbs/ft^3$ (0.29 $g/cm^3$). The shapes and sizes of the extrudates, as well as the results are shown in Table I. Dry samples of each catalyst were charged into a laboratory autoclave equipped with a turbine agitator.

Each catalyst was activated (resulting in the reduction of the copper in the catalyst) in the wet mode using technical grade 2-ethylhexanal. The ethylhexanal was passed over the catalyst at ambient temperature and atmospheric pressure while maintaining a small flow of nitrogen gas. The autoclave was then slowly pressurized to 1030 psig with hydrogen over a period of 15 minutes and the catalyst was heated at 120°-130° C. for 4 hours while maintaining a hydrogen flow rate of 312 GHSV.

After activation, the autoclave was evacuated to 6 psia and the feedstock (2-ethyl hexanal) was charged to the autoclave. After purging with nitrogen, the autoclave was pressurized with hydrogen to 1000 psig and the agitator was turned on and adjusted to rotate at 1500 rpm. The temperature was raised to 150° C. where it was held for 2 hours. Samples were taken at the start of the run and upon completion.

The catalyst activity was determined by comparing the percent of feedstock present in the product at the end of the 2 hour run with the percent of feed left when using the barium stabilized catalyst (Sample H). The results are shown in the following Table with the activity of this commercial catalyst being assigned an arbitrary value of 100.

TABLE 1

| Catalyst Samples | Size | Shape | Composition | Percent Activity |
|---|---|---|---|---|
| A | 3/16" | Cylindrical | 70% CuCr/30% $Al_2O_3$ | 115 |
| B | ⅛" | Cylindrical | 70% CuCr/30% $Al_2O_3$ | 161 |
| C | 1/16" | Cylindrical | 70% CuCr/30% $Al_2O_3$ | 242 |
| D | 1/32" | Cylindrical | 70% CuCr/30% $Al_2O_3$ | 577 |
| E | 1/20" | 4 flutes | 70% CuCr/30% $Al_2O_3$ | 354 |
| F | 1/20" | 4 flutes | 66% CuCr/4% MnO 30% $Al_2O_3$ | 370 |
| G | ⅛" | Cylindrical | 50% CuCr/50% $Al_2O_3$ | 147 |
| H | ⅛" | Tablet | 93 CuCr/7 Ba | 100 |

As a minimum, the catalysts of the present invention showed an activity that was substantially better than that of the ⅛" tablet (Sample H), with Sample B, an extrudate having the same size and shape as the tablet showing a 61% higher activity. The results also showed that the activity for the 70% copper chromite/30% alumina (Sample B) in a ⅛" extrudate was higher than it was for a 50/50 blend (Sample G). Also noted was a substantial increase in activity as the diameter of the extrudate decreases. The ⅛" tablet is as small as can be attained on most conventional tabletting machines whereas the extrudates of the present invention can be made at least as small as 1/32" in diameter with a corresponding increase in activity.

EXAMPLE II

Three different samples of the catalyst of this present invention were used for the vapor phase hydrogenation of n-butyraldehyde to butanol. All three samples were ⅛" round extrudates having a composition of 70% copper chromite and 30% Kaiser Versal 250. The samples were prepared according to the procedure described in Example I. They were distinguishable from one another in the following respects:

Sample K—calcined at 375°–385° C.—reduced and air stabilized

Sample L—calcined at 536° C.—unreduced

Sample M—calcined at 806° C.—unreduced

The average amount of n-butyraldehyde in the feedstock was 22.5%, with the balance being n-butyl alcohol.

The catalysts were activated as follows: Each catalyst was charged into a pressure reactor which was pressurized with nitrogen to an operating pressure of 130.5 psig. The aldehyde feedstock was flowed through the catalyst bed at a liquid hourly space velocity of 0.40 hours$^{-1}$ for a period of 30 minutes. The catalyst was then heated for 3½ hours until the inlet temperature reached 120° C.

Following activation, the catalyst was tested under the following process conditions:

Inlet temperature—120° C.–150° C.
Inlet pressure—130.5 psig
Hydrogen flow rate—993.5/hour GHSV
H$_2$/aldehyde weight ratio—1.20–1.25/1

Samples K and L were run first at 120° C. inlet temperature and then again at 150° C. while Sample M was run at 120° C. only. The operating conditions and analytical data for the feedstock end products are shown in Table II.

TABLE II

|  | Sample K | | | | Sample L | | | | Sample M | |
| --- | --- | --- | --- | --- | --- | --- | --- | --- | --- | --- |
|  | Run 1 | | Run 2 | | Run 1 | | Run 2 | | Run 1 | |
| Inlet Temperature | 120 | | 150 | | 120 | | 150 | | 120 | |
| Average Bed Temperature | 140 | | 167 | | 143 | | 171 | | 142 | |
| Analytical Data | Feed | Product | Feed | Product | Feed | Product | Feed | Product | Feed | Product |
| Normal Butyl Aldehyde | 23.5 | 0 | 21.87 | 0 | 23.49 | .19 | 22.16 | .02 | 22.75 | .19 |
| Normal Butyl Alcohol | 44.61 | 62.09 | 42.98 | 64.12 | 44.32 | 64.59 | 41.88 | 66.39 | 44.36 | 63.98 |
| I-Butyl Alcohol | 24.72 | 22.17 | 23.89 | 23.18 | 24.71 | 23.33 | 23.48 | 23.72 | 24.68 | 23.06 |
| Ethers | 0.38 | 1.82 | 0.39 | 6.30 | 0.48 | 1.20 | 0.34 | 5.26 | 0.42 | 0.89 |
| Light Ends | 0.08 | 0.06 | 0.08 | 0.08 | 0.08 | 0.06 | 0.07 | 0.07 | 0.07 | 0.06 |
| Heavy Ends | 5.48 | 12.43 | 9.31 | 4.85 | 5.26 | 9.41 | 10.16 | 3.34 | 6.34 | 10.47 |
| Total Carbonyls | 26.2 | 3.46 | 26.6 | 0.67 | 25.5 | 2.86 | 25.8 | 0.48 | 25.6 | 3.31 |

Referring to Table II, it is noted that the catalyst gives a high rate of conversion, in excess of 99%. Furthermore, it is noted that the calcination temperature of this novel catalyst does not seriously affect the performance of the catalyst. The reaction temperature has several effects on product mix and yield, the most notable of which are as follows: (a) as the temperature goes up the percent of carbonyls, (aldols, esters, acids, ketones and unreacted aldehydes) and heavy end fractions goes down, and (b) the formation of light ends is virtually nil at low and high temperatures.

These examples are intended to be illustrative of the invention but not limiting thereof. There are other variations that can be made in the method of manufacturing this catalyst and/or in the composition without departing from the scope of the invention. For example, a small amount, up to 15%, of silica (SiO$_2$) can be added to the catalyst blend along with the alumina, either to replace a portion of the alumina or as a supplement thereto. Furthermore, up to 10% of a stabilizer such as barium, or manganese may be added to the extrudable catalyst mix without departing from the teachings of the present invention.

A single screening test to determine whether a given sample of alumina can be blended with copper chromite to form an extrudable catalyst mix is described as follows. Thirty parts by weight of powdered alumina is blended with seventy parts of Cu 1106 P, a powdered copper chromite catalyst sold by Harshaw/Filtrol Partnership. A peptizing agent such as nitric acid or other mineral acid, or an organic acid such as acetic or formic acid is added to the mix after which the mix is forced through a 1/16" orifice of a Carver press or a Bonnot extruder. The extruded material is dried and calcined and is tested to determine crush strength and attrition resistance. If these physical properties are satisfactory and the catalyst suffers no loss of activity as compared to starting material, the alumina is regarded as a satisfactory replacement for a portion of the copper chromite.

We claim:

1. An extruded copper chromite/alumina catalyst prepared from a blend of between about 40% and about 82% by weight of copper chromite having the formula CuO:CuCr$_2$O$_4$ and between about 60% and about 18% by weight of an extrudable form of alumina wherein portions or all of the copper oxide and copper chromite are present in the reduced state, said catalyst having a surface area between about 20 m$^2$/g and about 225 m$^2$/g, and a packed apparent bulk density of between about 0.70 and about 1.20 g/cc.

2. The catalyst of claim 1 wherein at least 25% of the extruded alumina is selected from the group consisting of pseudoboehmite and α hydroxy boehmite.

3. The catalyst of claim 2 wherein the copper chromite is present in an amount of between 60% and 80% and the alumina is present in an amount of between 40% and 20%.

4. The catalyst of claim 3 in which all of the alumina, before calcination, has a pseudoboehmite structure.

5. The catalyst of claim 4 wherein the copper chromite is present in an amount of between about 68% and 72% and the alumina is present in an amount of between 32% and 28%.

6. The catalyst of claim 5 including up to 10% by weight of a stabilizer selected from the group consisting of barium and manganese.

7. The catalyst of claim 1 wherein the reduced copper is stabilized.

8. The catalyst of claim 1 wherein up to 15% of the alumina is replaced by silica.

9. A method of preparing an extruded copper chromite/alumina catalyst comprising:
  (a) blending from between about 18% to about 60% by weight alumina capable of being readily extruded, with between about 82% and about 40% by weight of copper chromite, between about 3% and about 7% by weight, based on alumina of a peptizing agent, and sufficient water to give an extrudable mix,
  (b) extruding the mix, and
  (c) calcining and reducing the extrudate.

10. The method of claim 9 wherein at least 25% of the alumina has a structure selected from the group consisting of a pseudoboehmite structure and an α hydroxy boehmite structure.

11. The method of claim 9 wherein the catalyst contains up to 10% of a reduction stabilizer consisting of a salt of a metal selected from the group consisting of barium and manganese.

12. The method of claim 9 wherein water is added to step (a) in an amount which will give a loss on ignition of between about 37% and about 39% during calcination.

13. The method of claim 9 wherein the calcined catalyst is reduced following calcination.

14. The method of claim 13 wherein the reduced catalyst is air stabilized.

15. The method of claim 9 wherein the peptizing agent is a mineral acid.

16. The method of claim 9 wherein the peptizing agent is an organic acid.

* * * * *